(12) United States Patent
Friedrich

(10) Patent No.: US 11,478,615 B2
(45) Date of Patent: Oct. 25, 2022

(54) SECUREMENT DEVICE WITH INTEGRATED INTRA-LUMINAL ELECTRO-CONDUCTION AND EXTERNAL TAMPER SENSITIVITY

(71) Applicant: Novum Vascular, LLC, San Antonio, TX (US)

(72) Inventor: Terrell Friedrich, Helotes, TX (US)

(73) Assignee: NOVUM VASCULAR, LLC, San Antonio, TX (US)

(*) Notice: Subject to any disclaimer, the term of this patent is extended or adjusted under 35 U.S.C. 154(b) by 195 days.

(21) Appl. No.: 16/879,634

(22) Filed: May 20, 2020

(65) Prior Publication Data

US 2020/0368497 A1    Nov. 26, 2020

Related U.S. Application Data

(60) Provisional application No. 62/850,478, filed on May 20, 2019.

(51) Int. Cl.
*A61M 25/02* (2006.01)
*A61F 13/02* (2006.01)

(52) U.S. Cl.
CPC .......... *A61M 25/02* (2013.01); *A61F 13/0216* (2013.01); *A61M 2025/0246* (2013.01); *A61M 2025/0273* (2013.01)

(58) Field of Classification Search
CPC .... A61M 2025/024; A61M 2025/0246; A61M 2025/0273; A61M 2205/18; A61M 2205/44; A61M 25/02; A61M 2025/0266
See application file for complete search history.

(56) References Cited

U.S. PATENT DOCUMENTS

2011/0190681 A1* 8/2011 Cazzini ............... A61M 1/3659
604/6.11

* cited by examiner

*Primary Examiner* — Deanna K Hall
(74) *Attorney, Agent, or Firm* — Kilpatrick Townsend & Stockton LLP

(57) ABSTRACT

A catheter securement device with integrated intra-luminal electro-conduction, and external tamper sensitivity, for tamper or movement detection. The catheter securement device accordingly can detect movement or tampering of an inserted catheter, which will allow a healthcare provider to take action to prevent movement or removal of the catheter from a patient.

11 Claims, 6 Drawing Sheets

Figure 1
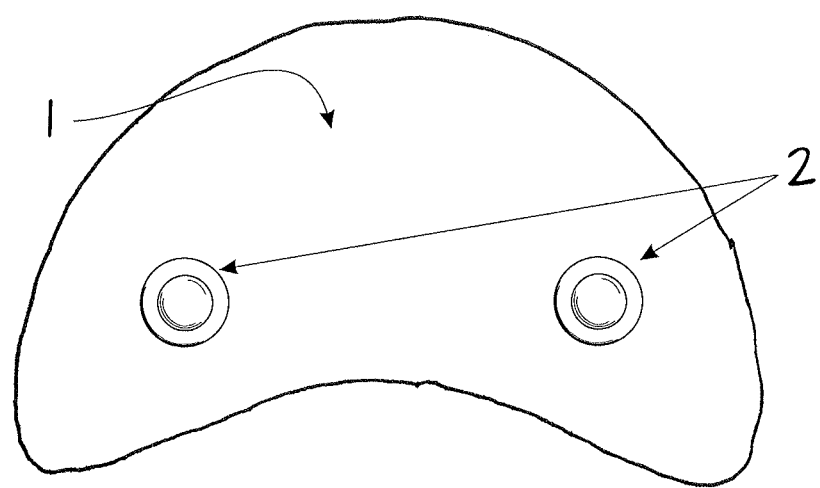
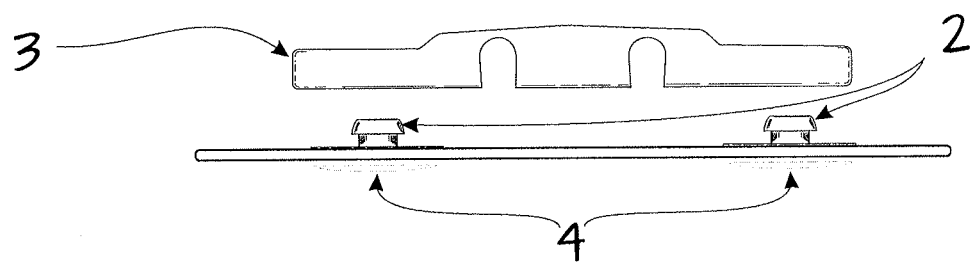
Figure 2

Front View

Top View

SECUREMENT DEVICE WITH INTEGRATED INTRA-LUMINAL ELECTRO-CONDUCTION AND EXTERNAL TAMPER SENSITIVITY

CROSS-REFERENCE TO RELATED APPLICATIONS

The present application claims the benefit of U.S. Provisional Application No. 62/850,478, filed May 20, 2019, and entitled "SECUREMENT DEVICE WITH INTEGRATED INTRA-LUMINAL ELECTRO-CONDUCTION AND EXTERNAL TAMPER SENSITIVITY", the entire contents of which are incorporated herein by reference.

BACKGROUND

The present invention relates to a catheter securement system for the prevention of removal or malpositioning a catheter that has been inserted into a patient. More specifically, the present invention relates to a catheter securement device with integrated intra-luminal electro-conduction, and/or external tamper sensitivity.

In the art relating to catheters, after insertion of a catheter through a patient's skin into a vein, the catheter must be secured to prevent the catheter from slipping out of the patient's vein. Commonly, surgical tape is used to hold the catheter hub or tubing connected to the catheter to the patient's skin. Oftentimes, this method is ineffective to permanently, securely anchor the catheter and to prevent catheter movement.

Moreover, it is also known to use a catheter dressing with pressure sensitive adhesives to fully secure and protect a catheter such as a Peripherally Inserted Central Catheter ("PICC"). PICCs are typically made of polyurethane or silicone based materials. Due to the low surface energy of silicones, adhesives from dressings do not fully anchor or grip to silicone substrates as well as polyurethane materials. Thus, PICC movement will occur when a PICC is tugged or pulled by a patient in whom the PICC is inserted, or by another person.

Further, inadvertent movement of a catheter while the catheter is inserted in a vein is a leading cause of premature catheter failure. When a catheter moves in a vein, it scrapes and pokes the inner wall of the vein, thereby irritating the vein. Repeated movement of the catheter thereby causes sufficient irritation of the vein to require the catheter to be removed and a new catheter inserted in a different location along the same vein or in an entirely new vein. This is costly as it results in a waste of resources. Also, repeated movement of an inserted catheter can cause migration of the catheter in the vein or worse, may lead to the catheter being removed from the vein.

Therefore, while a need exists for effective anchoring/securement devices for catheters, a further need exists for a device with tamper sensing and detection.

SUMMARY

This document presents a catheter securement device with integrated intra-luminal electro-conduction, and external tamper sensitivity, for tamper or movement detection. The catheter securement device accordingly can detect movement or tampering of an inserted catheter, which will allow a healthcare provider to take action to prevent movement or removal of the catheter from a patient.

In one aspect, a catheter securement device for securing a catheter to a site on a patient includes an adhesive pad having a bottom surface and a top surface. The bottom surface includes an adhesive for adhering to the site of the patient, and further includes one or more electrolyte coupling pads. The top surface includes one or more conductive connectors connected through the adhesive pad to a respective electrolyte coupling pad, and each of the one or more conductive connectors extend up from the top surface of the adhesive pad.

The catheter securement device further includes an upper securement shell that forms a cover having at least one opening to receive, cover and secure the catheter to the site on the patient. A top of the upper securement shell includes one or more conductive contacts extending from the top of the upper securement shell. A bottom of the upper securement shell includes at least one receptacle below each of the one or more conductive contacts, each of the one or more receptacles being configured to receive a respective one of the one or more conductive connectors extending from the top surface of the adhesive pad and to connect the respective conductive connector with a proximal end of the respective conductive contacts extending from the top of the upper securement shell.

The catheter securement device further includes an annunciator coupled with the one or more conductive contacts by an electrical signal conduit, the annunciator being configured to generate an alarm signal upon a disconnection between any conductive contact and the respective conductive connector, or between any conductive connector and the respective electrolyte coupling pad.

In another aspect, a catheter securement device includes an adhesive pad having a bottom surface and a top surface, the bottom surface having an adhesive for adhering to the site of the patient, the top surface having one or more connectors extending up from the top surface of the adhesive pad. The catheter securement device further includes an upper securement shell that forms a cover having at least one opening to receive, cover and secure the catheter to the site on the patient. A top of the upper securement shell includes one or more conductive contacts extending from the top of the upper securement shell. A bottom of the upper securement shell includes at least one receptacle configured to receive a respective one of the one or more connectors extending from the top surface of the adhesive pad.

The catheter securement device further includes a proximity sensor provided to the top of the upper securement shell configured to detect a proximity of an external object that could tamper with the catheter securement device. The catheter securement device further includes an annunciator coupled with the proximity sensor by an electrical signal conduit, and being configured to generate an alarm signal upon detection of the proximity of the external object.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIG. 1 is a top view of a securement system, in accordance with implementations of a securement system as described herein;

FIG. 2 is a side view of a securement system, in accordance with implementations of a securement system as described herein;

Like reference symbols in the various drawings indicate like elements.

DETAILED DESCRIPTION

This document describes a securement device with integrated intra-luminal electro-conduction, and external tamper sensitivity, as shown in FIGS. 1-11. The securement device can be applied to catheters, such as a Peripherally Inserted Central Catheter ("PICC"), which have been intravenously inserted into a patient and secured in place, such as by the securement device against the patient's skin proximate to the insertion point.

Referring in particular to FIGS. 1 and 2, a catheter securement device includes an adhesive pad (1) that is configured with conductive connectors (2) and electrolyte coupling pads (4). The adhesive pad (1) is configured to be mated with an upper securement shell (3).

The upper securement shell (3) includes one or more locations for connection to a device that senses electrical impulses. Such sensing device can be an electro-conduction sensor configured to sense a change of electronic signals that are conducted through a lumen that is part of the catheter.

Figure 3:
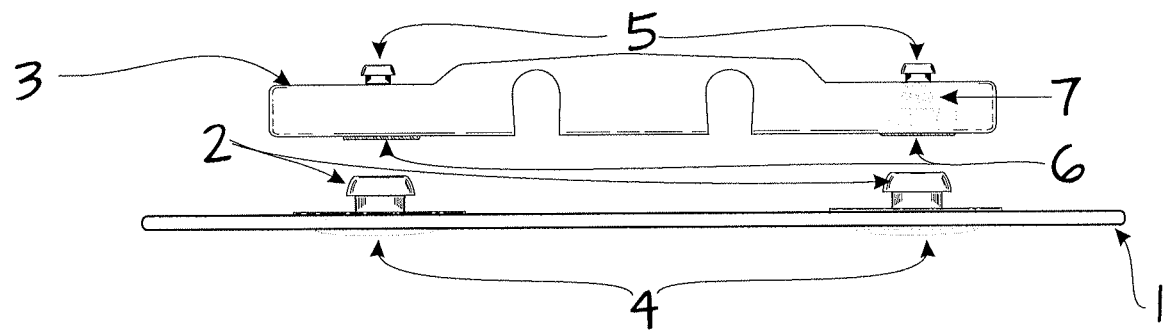
FIG. 3 is a side view of a securement system having lead wire connectors and one or more conductive fastener receivers, in accordance with implementations of a securement system as described herein.
Figure 4:
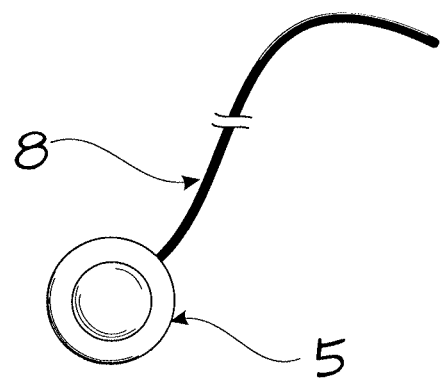
FIG. 4 illustrates an alternative lead wire configuration with pre-attached lead wire, in accordance with implementations described herein.

As shown in particular with reference to FIG. 3, inner flexible contact receptacles (6, 7) connect the securement shell (3) both physically and in an electrically conductive manner to the adhesive pad (1) and via the electrolyte coupling pads (4) to the patient's skin. Conductive contacts (5) on the top of the upper securement shell (3), and that connect to conductive connectors (2) via contact receptacles (6, 7), can be connected with a wire (8) or other electrical signal conduit, as shown in FIG. 4.

Figure 5:
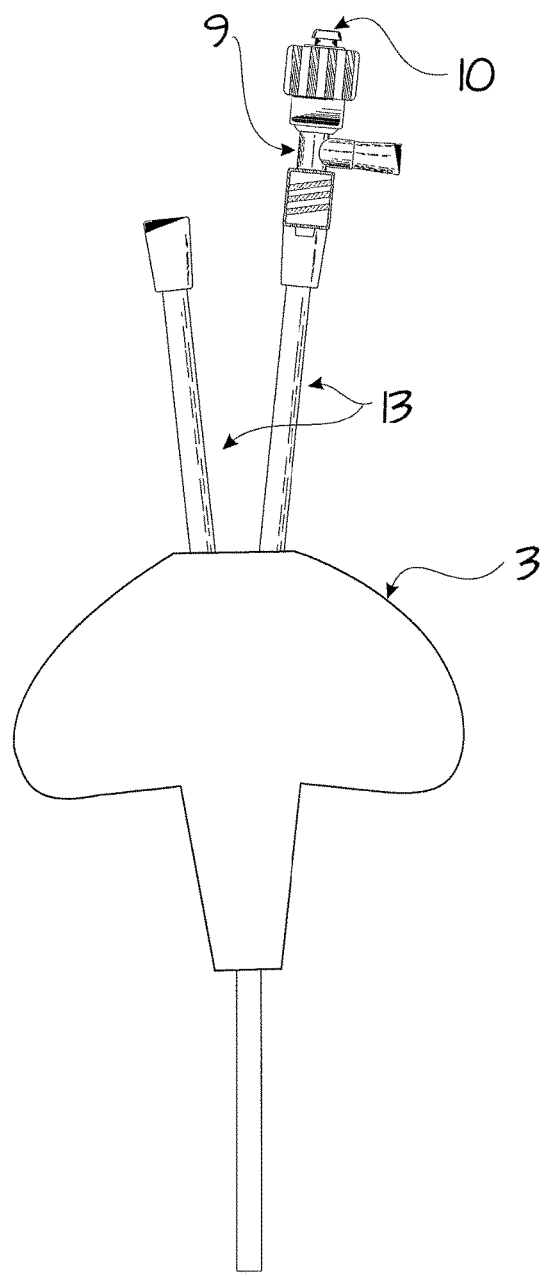
FIG. 5 shows a securement device with vascular access device extension tubing, in accordance with implementations described herein.
Figure 6:
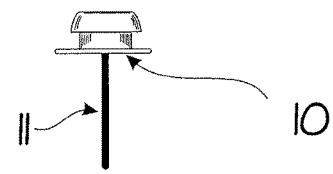
FIG. 6 shows a connector with an electrically conductive, non-corrosive connector element.
Figure 7:
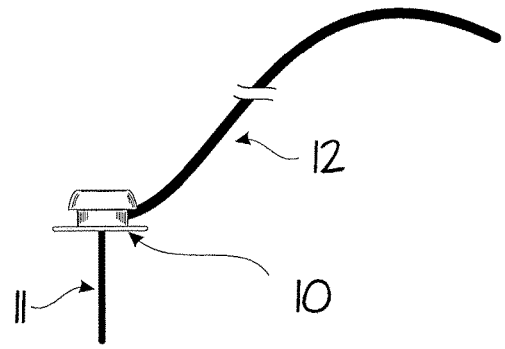
FIG. 7 shows a connector with an electrically conductive, non-corrosive connector element, with a pre-attached lead wire.
Figure 8:
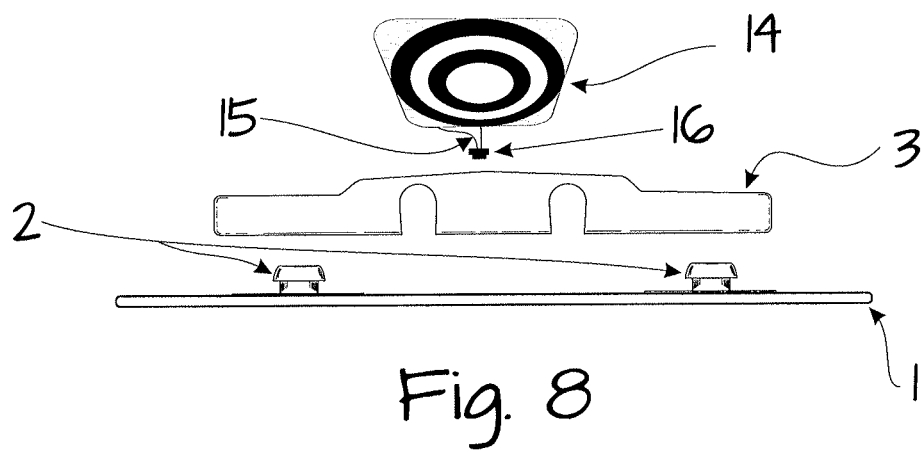
FIG. 8 is a front view of a catheter securement device with a proximity and/or contact sensor.
Figure 9:
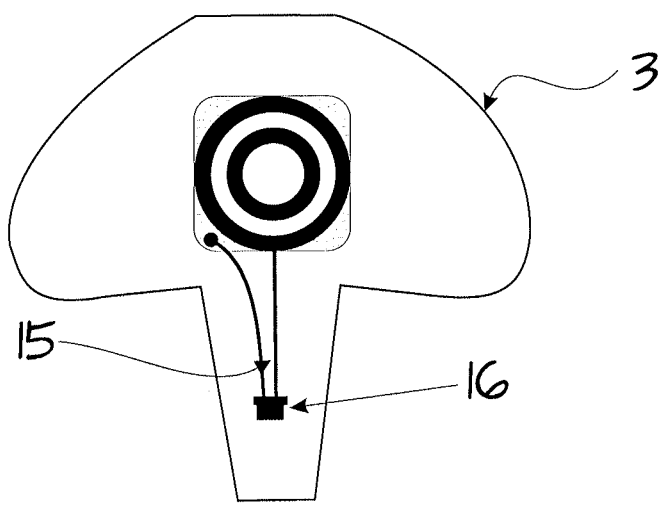
FIG. 9 is a top view of a catheter securement device with a proximity and/or contact sensor.
Figure 10:
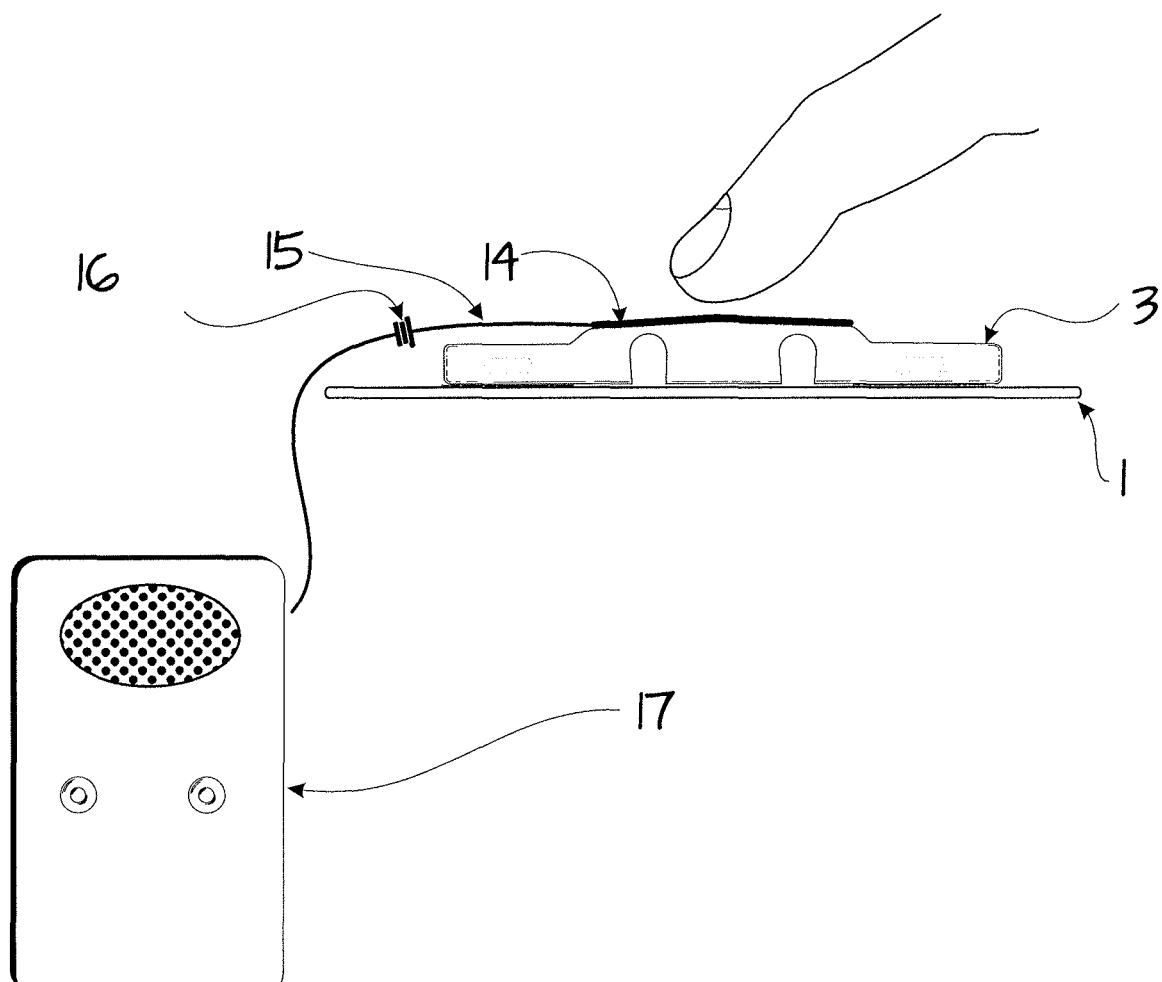
FIG. 10 shows a catheter securement device with a proximity and/or contact sensor, in use with an annunciator device in accordance with implementations described herein.
Figure 11:
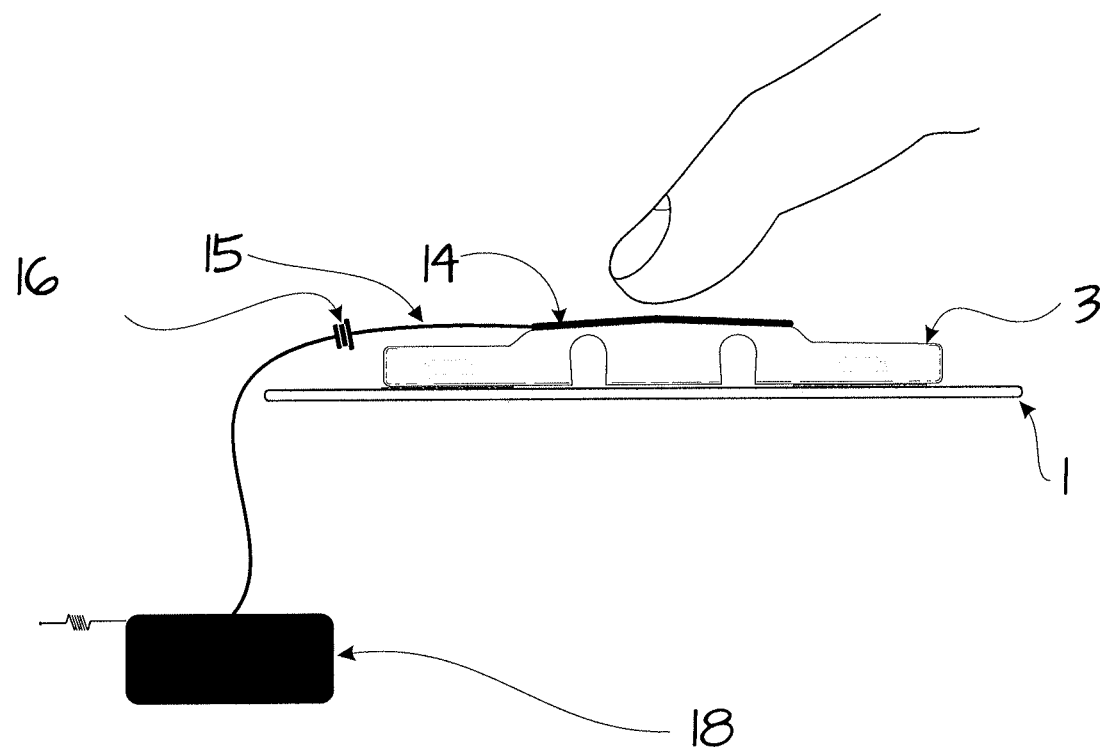
FIG. 11 shows a catheter securement device with a proximity and/or contact sensor, in use with a wireless transmitter or transceiver to communicate with one or more annunciator devices, in accordance with implementations described herein.
Figure 11:
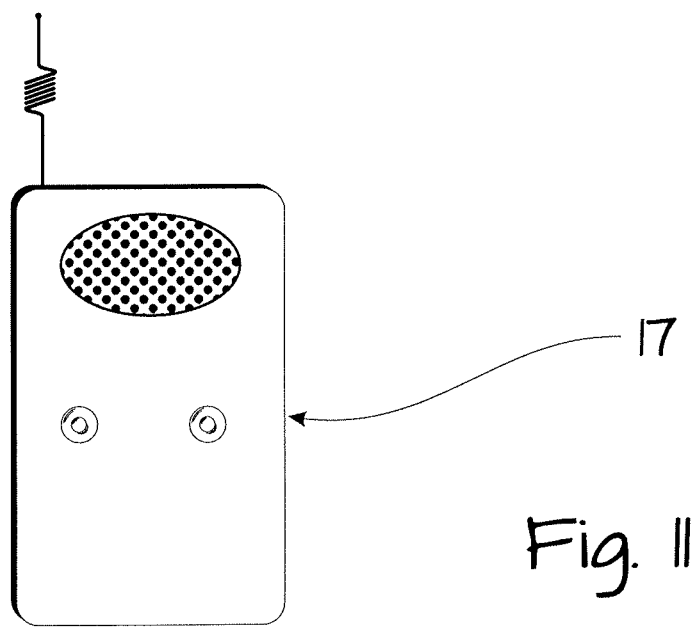

As best illustrated in FIGS. 5-7, a third lead is connected to device which senses electrical impulses via a connector (10) with a non-corrosive electrically conductive element (11) into and secured in place with an adapter, such as a commonly available Tuohy-Borst adapter, which are specifically designed to facilitate catheter introduction in interventional and diagnostic procedures where fluid backflow is a concern.

In some implementations, the electronic signals can be a set of regular electrical pulses applied to the lumen. In other implementations, the electronic signals can be a continuous signal applied to the lumen. The electronic signals can be transmitted in any of a wired transmission protocol or wireless transmission protocol. Further, the electronic signals can be encoded by a transmitter to maintain patient confidentiality, or to inhibit cross-signaling with other devices or signal transmissions. The electronic signals can include an identifier that identifies the securement device and/or the patient. The identifier can be associated with a code, such as an encrypted alphanumeric code or the like. In some implementations, the electronic signals can be relayed over one or more electronic signal repeaters, for applications such as telemedicine or the like.

When a disruption or change of any electronic signal occurs, such as by the patient pulling on, removing or attempting to remove, or otherwise tampering with the catheter and/or the catheter securement device, the catheter securement device can be configured to detect the disruption or change to generate an alert, such as an audible signal, a wireless alarm signal, a cellular radio connection, a visual signal, or the like.

As shown in FIGS. 8-11, the device can also be configured to include detection of tampering using a proximity sensor (14) bonded to the securement shell (3). The proximity sensor (14) is configured to detect a proximity of an external object, such as a hand or finger of the patient, which could be used to tamper with the securement device or the upper securement shell (3) thereof. The proximity sensor is connected via pre-connected lead wires (15) to a connector (16), which can be part of an annunciator (17). The annunciator (17) can generate an audio alarm, a visual alarm (such as a set of light-emitting diodes (LEDs) or a video signal for signaling a particular, predetermined pattern), or a graphical alarm, such as generating a call on a cellular or wireless radio transceiver (18) or transmitter, that is directed to a healthcare provider or practitioner and/or one or more annunciators (17).

The annunciator (17) can be a simple wireless transceiver or receiver employing any communication protocol for receiving the tampering detection signal, which can be a wired or wireless communication protocol. In some implementations, the annunciator (17) can be a mobile computing device having a computer processor that executes a local application for receiving, via a wireless protocol such as cellular, Wi-Fi or Bluetooth, the tampering detection signal and generating the alarm, which can be an audio alarm, a visual alarm, a haptic alarm such as a vibration, or any combination thereof.

Although a few embodiments have been described in detail above, other modifications are possible. Other embodiments may be within the scope of the following claims.

The invention claimed is:

1. A catheter securement device for securing a catheter to a site on a patient, the catheter securement device comprising:
   an adhesive pad having a bottom surface and a top surface, the bottom surface having an adhesive for adhering to the site of the patient, the bottom surface further having one or more electrolyte coupling pads, the top surface having one or more conductive connectors connected through the adhesive pad to a respective electrolyte coupling pad, each of the one or more conductive connectors extending up from the top surface of the adhesive pad;

an upper securement shell that forms a cover having at least one opening to receive, cover and secure the catheter to the site on the patient, a top of the upper securement shell having one or more conductive contacts extending from the top of the upper securement shell, a bottom of the upper securement shell having at least one receptacle below each of the one or more conductive contacts, each of the one or more receptacles being configured to receive a respective one of the one or more conductive connectors extending from the top surface of the adhesive pad and to connect the respective conductive connector with a proximal end of the respective conductive contacts extending from the top of the upper securement shell; and an annunciator coupled with the one or more conductive contacts by an electrical signal conduit, the annunciator being configured to generate an alarm signal upon a disconnection between any conductive contact and the respective conductive connector, or between any conductive connector and the respective electrolyte coupling pad.

2. The catheter securement device in accordance with claim 1, wherein the electrical signal conduit includes a lead wire connected with the one or more conductive contacts.

3. The catheter securement device in accordance with claim 1, wherein the electrical signal conduit includes a wireless transmitter connected with the one or more conductive contacts.

4. The catheter securement device in accordance with claim 1, further comprising a proximity sensor provided to the top of the upper securement shell configured to detect a proximity of an external object that could tamper with the catheter securement device, the proximity sensor being coupled with the electrical signal conduit.

5. The catheter securement device in accordance with claim 1, wherein the annunciator includes a mobile computing device having a computer processor that executes a tamper detection application for receiving an electrical signal upon the disconnection between any conductive contact and the respective conductive connector, or between any conductive connector and the respective electrolyte coupling pad, to generate a tamper detection alarm.

6. A catheter securement device for securing a catheter to a site on a patient, the catheter securement device comprising:

an adhesive pad having a bottom surface and a top surface, the bottom surface having an adhesive for adhering to the site of the patient and having one or more electrolyte coupling pads, the top surface having one or more connectors extending up from the top surface of the adhesive pad;

an upper securement shell that forms a cover having at least one opening to receive, cover and secure the catheter to the site on the patient, a top of the upper securement shell having one or more conductive contacts extending from the top of the upper securement shell, a bottom of the upper securement shell having at least one receptacle configured to receive a respective one of the one or more connectors extending from the top surface of the adhesive pad;

a proximity sensor provided to the top of the upper securement shell configured to detect a proximity of an external object that could tamper with the catheter securement device; and an annunciator coupled with the proximity sensor by an electrical signal conduit, the annunciator being configured to generate an alarm signal upon detection of the proximity of the external object.

7. The catheter securement device in accordance with claim 6, wherein the one or more connectors extending up from the top surface of the adhesive pad are conductive connectors.

8. The catheter securement device in accordance with claim 6, wherein each of the one or more receptacles is configured to receive a respective one of the one or more conductive connectors extending from the top surface of the adhesive pad and to connect the respective conductive connector with a proximal end of the respective conductive contacts extending from the top of the upper securement shell.

9. The catheter securement device in accordance with claim 8, wherein the annunciator is further configured to generate an alarm signal upon a disconnection between any conductive contact and the respective conductive connector, or between any conductive connector and the respective electrolyte coupling pad.

10. The catheter securement device in accordance with claim 9, wherein the electrical signal conduit includes a lead wire connected with the one or more conductive contacts.

11. The catheter securement device in accordance with claim 9, wherein the electrical signal conduit includes a wireless transmitter connected with the one or more conductive contacts.

* * * * *